Figure 1:
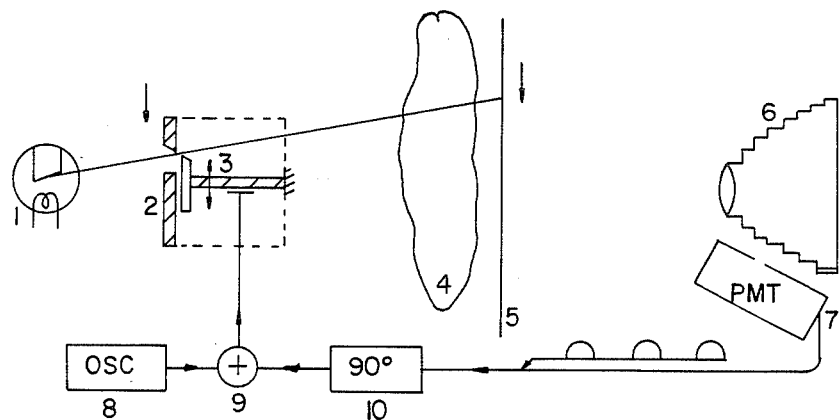

United States Patent [19]

Boersma

[11] Patent Number: 4,785,471

[45] Date of Patent: Nov. 15, 1988

[54] RADIOSCOPIC IMAGE DEVICE

[75] Inventor: Sipko L. Boersma, Delft, Netherlands

[73] Assignee: bv Optische Industrie De Oude Delft, Delft, Netherlands

[21] Appl. No.: 921,946

[22] Filed: Oct. 22, 1986

[30] Foreign Application Priority Data

Oct. 24, 1985 [NL] Netherlands ............... 8502910

[51] Int. Cl.⁴ ............................................. G21K 5/10
[52] U.S. Cl. ............................. 378/146; 378/145; 378/156; 378/157
[58] Field of Search .................. 378/145–147, 378/150–153, 156–158

[56] References Cited

U.S. PATENT DOCUMENTS 4,626,688 12/1986 Barnes ........................ 378/156
4,639,941 1/1987 Hounsfield ................... 378/19
4,675,893 6/1987 Duinker et al. ............... 378/145
4,677,652 6/1987 Duinker et al. ............... 378/145

*Primary Examiner*—Craig E. Church
*Assistant Examiner*—John C. Freeman
*Attorney, Agent, or Firm*—Louis E. Marn

[57] ABSTRACT

A radioscopic image former comprises a slit between an X-ray source and a subject to produce an X-ray fan beam to scan the subject. The transmission of the slit is adjusted locally during the scanning depending on local absorptions in the subject. The X-ray fan beam is cyclically modulated. The local modulation frequency depends on the coordinate in the longitudinal direction of the slit. The slit comprises a number of tongues each tongue being excited at or near its resonant frequency. Each tongue has its own frequency or phase and acts as a frequency-selective element.

5 Claims, 1 Drawing Sheet

RADIOSCOPIC IMAGE DEVICE

The invention relates to a radioscopic image former for producing X-ray photographs or electronic images of patients or other subjects capable of transmitting X rays.

For medical applications the contrast range is very large. If it is possible for the image to contain the complete contrast range, small differences in contrast are in danger of becoming invisible.

According to a known technique this is prevented by dividing the subject up into a number of small regions and then regulating the X-ray intensity in each small region so that the average image intensity transmitted is approximately equal in all the small regions. Fine details within a small region are then readily visible.

According to Vlasbloem (Dutch Patent Application No. 8,400,845) this is achieved by placing a slit between X-ray source and subject, which slit moves in a direction perpendicular to the longitudinal direction of the slit. The patient is thus scanned with a flat X-ray beam. One. (or 2) side(s) of the slit consists of a number (e.g. 20) of tongues of material which is opaque to X-rays. The tongues are electrically controlled and in this way regulate the local width of the slit. The control may be piezoelectric or electromagnetic.

As the horizontal slit scans the patient vertically, the slit section of each tongue will describe its own vertical track across the patient. Behind the patient there is an X-ray detector in the track of each tongue. The signal from each detector controls its own tongue via a feedback circuit. The intensity is thus kept constant behind the patient in the small region of each tongue.

The method has proved to work well.

There are, however, two practical drawbacks:

1. A large number of X-ray detectors are required,
2. each slit section (tongue) must be imaged on the correct, associated detector. As a result of this, there is no longer a free choice in the position of the image screen.

These drawbacks are avoided in the present invention. This is achieved by means of additional modulations of the X-ray beam.

The X-ray beam from each slit section is also modulated yet again periodically with respect to time ("chopped") and, indeed, each section is modulated with a different frequency. The position information is now contained in the time frequency and one X-ray detector is sufficient which sums the entire slit image. A row of detectors is no longer necessary. There is now furthermore a free choice in the siting of the image screen since the position information is contained in the time frequencies. Just as many frequencies may be chosen as there are small slit areas. But half the number may also be sufficient. Two small areas may be given the same frequency since, provided the X-ray modulations differ by 90° in phase, the signals can always be recovered.

The additional modulations may be brought about by one or more moving rasters in the X-ray beam.

But it is also possible to use Vlasbloem's electrically controlled tongues for this purpose. This will be explained by reference to drawings 1 to 4 incl.

FIG. 1 shows an X-ray source 1, a slit 2 which is cyclically exposed by the vibrating tongue 3, a subject 4, fluorescent screen 5, camera 6, photocell 7, phase shifter 10, oscillator 8 and summing device 9.

Figure 2:
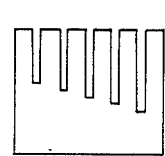

FIG. 2 shows a number of tongues with different resonance frequencies.

Figure 3:
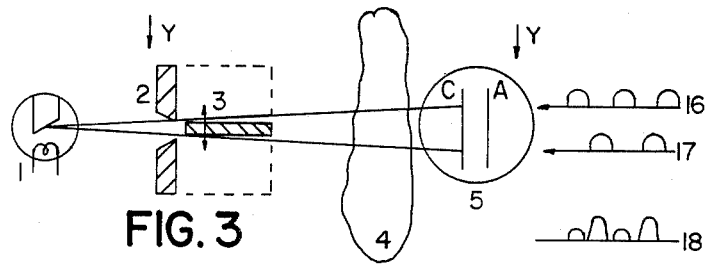

FIG. 3 shows an X-ray source 1, a slit 2 which can transmit X-ray radiation twice in each cycle of the vibrating tongue 3, a subject 4 and a tubular X-ray image intensifier tube 5. 16 and 17 are light intensities at the top and bottom of tube 5, 18 being the total intensity.

Figure 4:
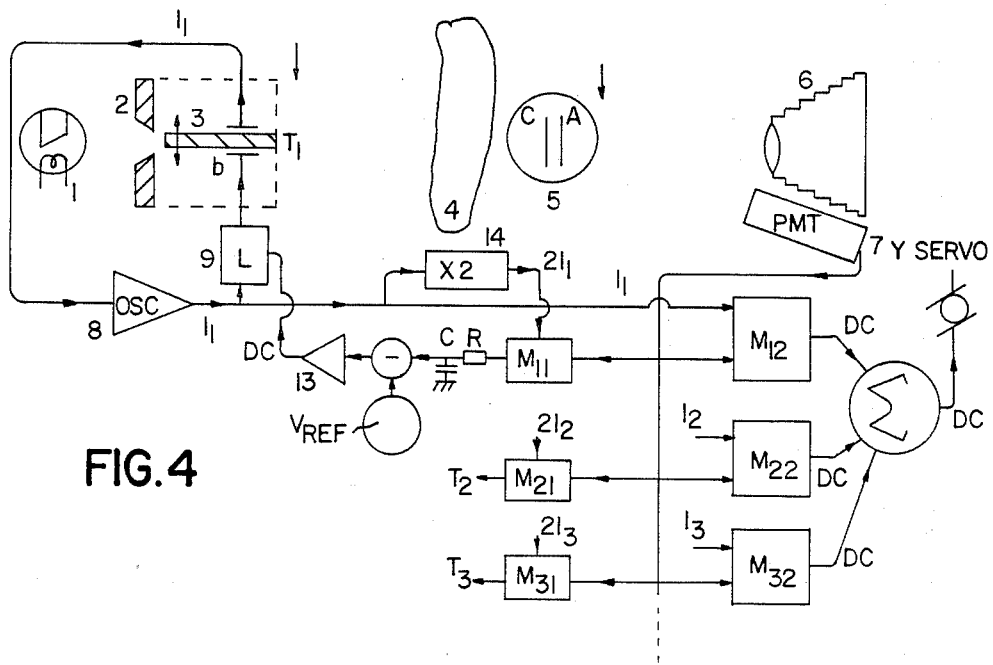

FIG. 4 shows an arrangement of FIG. 3 with camera 6, photocell 7, self-oscillating tongue oscillator 8 with limiter 9, frequency doubler 14, and modulators $M_{xx}$.

In FIGS. 1, 2 and 3 are sections through the slit and through one tongue, which in this case is excited piezoelectrically at its resonant frequency by oscillator 8. In its quiescent state tongue 3 precisely covers the slit 2. During oscillation a cyclically modulated X-ray beam is produced.

After passage through the patient and fluorescence of the screen 5, the output signal of the photomultiplier forms a series of pulses having the frequency of the tongue. The total signal from all the tongues together forms a spectrum.

This signal could be selectively detected in a number of detectors and the DC voltages produced used to adjust the respective tongues.

In this manner the result is achieved that the X-ray intensity behind the patient is approximately equally large in each small region. This means contrast compression for the low spatial frequencies in the image.

Instead of tongue adjustment, the detector signals can also be used to regulate the individual tongue amplitudes since the average X-ray intensity is more or less proportional to the amplitude of vibration. This latter method, i.e. amplitude regulation, has been used. in FIG. 1. In FIG. 1 no separate selective detectors are used. In this case these are the tongues themselves. After suitable phase shift the composite signal from all the tongues supplied from 7 is fed back to all the tongues. As a result of resonance, each tongue only responds to that frequency component in the signal which it has itself produced. The said component forms a damping term for said tongue which reduces its vibration amplitude and consequently also the average X-ray transmission. The damping is larger at points where there is little X-ray absorption since the tongue vibrates less and the beam is more strongly attenuated.

If the tongue spectrum is so chosen that it comprises less than one octave, the signal may be distorted.

A set of tongues with different resonant frequencies is shown in FIG. 2. If there are N tongues, the oscillator 8 and the summing device 9 in FIG. 1 appear N times but the photocell 7 and the phase shifter (and possibly an amplifier) only once.

The equipment in FIG. 1 is still subject to 2 drawbacks:

1. The slit transmits less than half the X-ray energy.
2. The X-ray beam flickers. The vertical scanning speed must be slow enough- that no lines appear in the image. The embodiments of the present invention in FIGS. 3 and 4 avoid said drawbacks.

In FIG. 3 the slit 2 is covered by the tongue 3 when the latter is in its quiescent state. When 3 vibrates, the slit transmits X-ray radiation 2 times per vibration cycle. The X-ray output is therefore twice as great as in FIG. 1. The flicker frequency is also twice as great and the slit can therefore scan the patient more rapidly before lines become visible in the image.

In FIG. 3 a tubular X-ray image intensifier is shown as "fluorescent screen". As the slit scans the patient from top to bottom, said tube must also move in order to remain in the flat beam.

Although the slit 2 transmits radiation 2 times per cycle, the transmission is spatially somewhat separated. Signal 6 is incident on the top half of tube 5 and signal 17 on the bottom half. If tube 5 is correctly positioned, no fundamental wave appears in the total signal 18.

During the scanning, tube 5 has to follow the movement of slit unit 2, 3. If it does not, fundamental wave is produced in the total signal, from which a phasesensitive detector can derive an error signal for a position servo.

The signal 18, which has the frequency 2f, now has to control the amplitude of the tongue having frequency f. This cannot be done by means of the simple coherent feedback in FIG. 1 since the signal and tongue frequencies are different. Coherent feedback is, however, quite possible if there is a balance modulator for each tongue, which modulator transposes the signal downwards by the frequency f, the control frequency of the tongue. A tongue responds only to that term in the product of mixing which corresponds to the tongue frequency. Provided it is of correct phase, this is a damping term for said tongue. All of this is completely analogous to FIG. 1.

But just as incoherent feedback would be possible in FIG. 1, it is also possible here. An incoherent control of the tongue vibration amplitude is shown in FIG. 4. The piezoelectric tongue 3 is incorporated in a self-oscillating manner in the feedback circuit 3, 8, 9 (9 is a limiter). The frequency of the tongue $T_1$ shown is $f_1$. The said tongue produces in the photocell 7 a frequency $2f_1$ which will have to control the tongue amplitude, and a signal having frequency $f_1$ which is capable of controlling the position servo as described earlier.

The modulator $M_{12}$ produces DC from the signaL having frequency $f_1$ for the benefit of the position servo. The modulator $M_{11}$ having switching frequency $2f_1$ produces DC from the signal component having frequency $2f_1$. At the output of the low pass filter RC a DC voltage is produced which regulates the tongue amplitude via limiter 9. Other tongues having other frequencies in their photocell signal do not produce DC in the mixer $M_{11}$.

In this case, therefore, the selective element is not the tongue itself, but the homodyne mixer $M_{11}$ together with the low pass filter. If there are N tongues, there have also to be N amplifiers 8 and N limiters 9, one photocell 7, N mixers $M_{12}...M_{N2}$, N doublers 14, N error amplifiers 13, one reference voltage but N subtraction circuits.

The position servo modulators $M_{12}...M_{22}$ etc. do not have to be present in N-fold.

In FIG. 4 each tongue has its own oscillator. But it is also possible to dimension the tongues so that their resonant frequencies are all multiples of a low fundamental frequency. One set of pulses with this low fundamental frequency can then be used to excite all the tongues.

With satisfactorily dimensioned tongues it is also possible to derive the oscillator signals from an integrated circuit such as has been developed for electronic organs.

I claim:

1. An apparatus for slit radiography, which comprises:
    an X-ray source;
    an X-ray detector for sensing radiation pasing through a body to be radiographed;
    a slit diaphragm positioned between said X-ray source and said body for forming a substantially planar X-ray beam;
    a plurality of attenuating elements positioned along said slit diaphragm forming corresponding number of attenuating sections;
    means to move said elements within said X-ray beam;
    means for scanning said body with said planar X-ray beam;
    detection means co-operating with said X-ray detector and being responsive to radiation sensed by said X-ray detector to prodice an electric signal representative of intensity of the sensed radiation; and
    means for controlling said means to move said attenuating elements during 'scanning of said body in response to said electric signal, such that the movement of each attenuating element modulates for each corresponding section, the intensity of X-ray radiation at a certain temporal frequency, wherein each attenuating element moves in response to a different frequency or phase than all other attenuating elements.

2. The apparatus as defined in claim 1 wherein said attenuating elements comprises a plurality of tongues and wherein said means for controlling said attenuating elements to modulate the intensity of said X-ray radiation comprises means for exciting each tongue to vibrate at or near resonant frequency.

3. The apparatus as defined in claim 2 wherein said means for controlling the means to move said attenuating sections comprises frequency selective circuits.

4. The apparatus as defined in claim 3 wherein said frequency selective circuits include said tongues.

5. The apparatus as defined in claim 2 and further including means to control vibrational amplitudes of said vibrating tongues.

* * * * *

UNITED STATES PATENT AND TRADEMARK OFFICE
CERTIFICATE OF CORRECTION

PATENT NO. : 4,785,471
DATED : November 15, 1988
INVENTOR(S) : SIPKO LUU BOERSMA It is certified that error appears in the above-identified patent and that said Letters Patent is hereby corrected as shown below:

Column 4, line 15, "pasing", should read -- passing --.

Column 4, line 28, "prodice", should read -- produce --.

Column 4, line 40, "comprises", should read -- comprise --.

Signed and Sealed this

Eighteenth Day of July, 1989

Attest:

DONALD J. QUIGG

Attesting Officer

Commissioner of Patents and Trademarks